United States Patent [19]

Sausa et al.

[11] Patent Number: 5,364,795
[45] Date of Patent: Nov. 15, 1994

[54] LASER-BASED DETECTION OF NITRO-CONTAINING COMPOUNDS

[75] Inventors: Rosario Sausa, Bel Air; Josef Simeonsson, Elkridge; George Lemire, Bel Air, all of Md.

[73] Assignee: The United States of America as represented by the Secretary of the Army, Washington, D.C.

[21] Appl. No.: 28,088

[22] Filed: Jun. 11, 1993

[51] Int. Cl.$^5$ .......................................... G01N 33/22
[52] U.S. Cl. .................................. 436/106; 436/110; 436/116; 436/153; 436/172; 73/35; 250/461.1
[58] Field of Search ................. 436/116–118, 436/153, 172, 106, 110; 73/35; 250/461.1

[56] References Cited

U.S. PATENT DOCUMENTS

| | | | |
|---|---|---|---|
| 3,826,920 | 7/1974 | Woodroffe et al. | 250/461.1 |
| 4,066,904 | 1/1978 | Bertaux et al. | 250/372 |
| 4,315,753 | 2/1982 | Bruckenstein et al. | 422/83 |
| 4,775,633 | 10/1988 | Rounbehler | 436/106 |
| 5,094,815 | 3/1992 | Conboy et al. | 422/82 |
| 5,123,274 | 6/1992 | Carroll et al. | 436/156 |

OTHER PUBLICATIONS

Asscher et al. "Two–Photon Excitation as a Monitoring Technique for Photodissociation Dynamics: ($F_3NO_{-7}CF_{3+}NO(v,J)$", J. Chem Phys 72(1) 1980, pp. 768–769.

Rodgers et al. "Photofragmentation Laser Induced Fluorescence: A New Method for Detecting Atmospheric Trace Gases" Applied Optics, v 19 No. 21, 1980, pp. 3597–3605.

Mukhtar et al. "Photodissociation of Positive Molecular Ions of Nitrobenzene" Organic Mass Spectrometry v. 15, No. 1 1980 pp. 51–52.

Rockney et al. "Resonant Multiphoton Ionization Detection of the $NO_2$ Fragment from Multiphoton Dissocation of $CH_3NO_2$" Chem. Phys Letters v 79, No. 1, 1981 pp. 15–18.

Bunn et al. "Photodissociation of the Energy Selected Nitrobenzene Ion" J. Chem. Phys. 84(3) 1986 pp. 1424–1431.

Nobel et al. "Photodissociation of Jet Cooled $(CH_3)_3CNO$: Temporal Separation of Radiation Less Transitions and Unimolecular Reactions" J. Chem Phys. 84(6) 1986. pp. 3573–3574.

Primary Examiner—James C. Housel
Assistant Examiner—Jan M. Ludlow
Attorney, Agent, or Firm—Saul Elbaum; Freda L. Krosnick

[57] ABSTRACT

An apparatus and method for the sensitive detection of atmospheric and/or surface absorbed nitrocompounds has been developed. The apparatus and method may be employed to detect the presence or absence of propellants, explosives, and nitropollutants. The unique feature herein is that the apparatus and method employ one laser operating at or near 226 nm. The laser photofragments the target molecule and facilitates the detection of the characteristic NO fragment, by resonance-enhanced multiphoton ionization (REMPI) and/or laser-induced-fluorescence (LIF) via its $A^2\Sigma^+ - X^2\Pi_i$ transitions. The analytical utility of this apparatus and method has been demonstrated on numerous compounds, such as, DMNA, nitromethane, nitro-benzene, TNT, and RDX. With the present system, a limit of detection of 8 and 24 ppb is obtained for RDX and TNT, respectively, using only 100 micro-Joules per pulse of laser energy. Limits in the sub parts-per-trillion are projected using higher laser energies and improved system design.

16 Claims, 5 Drawing Sheets

| Compound | Limit of Detection (ppb) |
|---|---|
| NO | 8 |
| $NO_2$ | 240 |
| $CH_3NO_2$ | 1000 |
| DMNA | 450 (2000)[a] |
| RDX[b] | 8 |
| TNT[b] | 24 |
| Nitrobenzene | 2400 |

[a] Limit of detection obtained by laser-induced fluorescence of NO via its $A^2\Sigma^+ - X^2\Pi$ (0,0) transition

[b] In the analysis of RDX and TNT the pulsed valve was heated to 100°C.

FIG. 5

LASER-BASED DETECTION OF NITRO-CONTAINING COMPOUNDS

GOVERNMENTAL INTEREST

The invention described herein may be manufactured, used and licensed by or for the U.S. Government without payment to us of any royalty thereon.

BACKGROUND OF THE INVENTION

The present invention relates to an apparatus and method for detecting trace amounts of nitrocompounds. It provides a novel means for in situ detection of the presence of $NO_x$ containing compounds, wherein x is greater or equal to one, in the atmosphere or on various surfaces. The invention has been developed in order to monitor the presence of energetic materials, such as propellants and explosives, and nitropollutants in various environments.

Detection and monitoring of trace amounts of energetic materials is critical to the security and safety of the population. It is of particular interest in the areas of detecting potential terrorist activity, demilitarization and mine countermeasures. As a result of interest in this area, numerous methods and devices have been developed to reduce the risk to the general population by detecting the presence of said materials and preventing their use. The techniques which have been previously developed and employed are summarized in an article by A. Fainberg, entitled "Explosives Detection for Aviation Security," Science, Vol. 255, p. 2531 (March 1992).

The techniques previously employed include x-ray detection and nuclear techniques, such as thermal neutron analysis and nuclear resonance absorption. These techniques have been found to be applicable in the sensing of concealed energetic materials found in luggage or other containers. However, it is extremely difficult to detect the presence of dangerous chemicals—i.e. explosives—when carried by a person. Due to the health risks in exposing a human to x-rays and nuclear techniques, authorities are unable to monitor people in the same fashion or as thoroughly as they can luggage or other containers.

The above described prior art techniques are used to physically detect the presence of the target compounds. However, other prior art methods do exist which serve the purpose of detecting the presence of the target compounds'vapors in the atmosphere. Among the prior art vapor sensing techniques employed are gas chromatography/chemiluminescence, quadrupole mass spectrometry, ion mobility spectrometry, and animals, such as sniffing dogs.

Although these techniques appear attractive since they are capable of atmospheric vapor analysis, their applications are limited. For instance, when one employs the sensing method of gas chromatography/chemiluminescence, the response time before the results are obtained is lengthy, while quadrupole mass spectrometry is limited in that it suffers from nonselective ionization, that is all the species entering the ionization region are ionized and transmitted into the mass spectrometer. An additional technique previously employed is ion mobility spectrometry. This method is extremely sensitive (parts per trillion (ppt) range) and has a relatively short response time (seconds). However, this method is not quantitatively as accurate as the others since the signal dependence on concentration is non-linear, particularly in the tens of parts-per-billion (ppb) range. Moreover, with ion mobility spectrometry, clustering of the target molecules with water, competition for protonation with contaminants, and low mass spectroscopic resolution are problems frequently encountered.

The final prior art method to be discussed for detecting the presence of the specific materials of interest in the atmospheric vapor is the use of canines. The dog is the original vapor detector, or sniffer. Authorities still employ dogs to sweep buildings or sniff luggage or parcels to assure the absence or detect the presence of explosives therein. The use of dogs for these purposes is limited due to the fact that they are subject to fatigue, behavioral variations (good days/bad days), and the need for reinforcement and retraining. Although canines are very sensitive to the presence of specific vapors, they are subject to various outside factors. Therefore, it is critical to develop an efficient technological method for detecting specific vapors wherein said method is not effected by the detrimental factors set forth above. It is these factors which reduce the effectiveness of the method employed.

The present invention makes use of laser technology for the detection of trace atmospheric nitro compounds. Although lasers are not commonly employed in the detection of energetic materials of the type discussed above, they have been employed in the remote and in situ detection of toxic and non-toxic pollutant gases. In particular, a mobile light detection and ranging system (LIDAR) has been employed to detect NO and $NO_2$ in the ppb ranges at distances of less than 10 kilometers. This absorption method detects NO and $NO_2$ only, and not the energetic nitrocompounds which contain these functional groups. It employs the technique of differential absorption and is used commonly for remote detection. Many large molecules including energetic materials are difficult to detect spectroscopically using this technique due to the lack of distinguishing structure or absence of any absorption features in the ultraviolet-visible (UV-VIS) spectral region.

Although this laser technique has been used in the remote and in-situ detection of pollutant gases, the LIDAR methods are based on laser absorption which is a fundamentally different measurement as well as a less efficient means of detection than that employed herein. The present invention is for point detection and utilizes a laser differently than in the LIDAR technique. The invention herein employs a laser to both generate local levels of $NO/NO_2$ fragments from nitrocompounds and for the ionization is the NO fluorescence and/or ionization of NO that is being monitored to determine the presence of energetic nitrocompounds. This is accomplished using a photodetector and/or ion detector.

Accordingly, the present invention satisfies the recognized need for the development of a technological device capable of detecting trace amounts of atmospheric and surface-adsorbed nitrocompounds of the types discussed above, wherein said device and method employing the device are both accurate and efficient. The present invention is designed to effectively reduce the risk factor described—i.e., the presence of explosives, mines, etc.

BRIEF DESCRIPTION OF THE INVENTION

The present invention relates to the sensitive detection and monitoring of trace amounts of $NO_x$ containing compounds which may be found in atmospheric vapors and/or adsorbed onto various surfaces. Among the types of compounds which the present invention is designed to detect are propellants, explosives, and various pollutants.

The instrument employed herein is an integrated system comprising a sampling chamber, a detection system, and a control and data processing system. The present invention is highly specific to nitrocompounds and can be readily manufactured into a sturdy and fieldable device.

Central to the present invention is a laser which operates at or near 226 nm. It serves a dual function. First, it is used to photodissociate the target molecule into $NO_2$ and its companion radical; and second, it facilitates the detection of the characteristic fragment NO, formed from the rapid predissociation of $NO_2$, by resonance-enhanced multi-photon ionization (REMPI) and/or laser-induced-fluorescence (LIF) via its $A^2\Sigma^+ - X^2\Pi^i$ electronic transitions. The novelty of the present invention resides in this feature.

The present invention has been demonstrated on a number of nitrocompounds such as $NO_2$, dimethylnitramine (DMNA), nitromethane, nitrobenzene, trinitrotoluene (TNT), and 1,3,5-trinitrohexahydro-1,3,5-triazine (RDX).

The present invention provides an apparatus and method for detecting and monitoring atmospheric and surface adsorbed $NO_x$ containing compounds using a single laser operated at or near 226 nm.

Accordingly, it is an object of the present invention to provide a laser-based sensitive detection apparatus for monitoring and detecting the presence of trace amounts of nitrocompounds present in atmospheric vapors.

It is a further object of the invention to provide an apparatus for detecting trace amounts of atmospheric vapors of nitrocompounds, wherein the nitrocompounds may be energetic materials such as explosives and/or propellants.

It is a further object of the present invention to provide a laser-based, ultra-sensitive detector apparatus capable of detecting atmospheric vapors of $NO_2$ containing pollutants.

It is a further object of the present invention to provide a laser-based sensitive detection apparatus wherein one laser operating at or near 226 nm is employed to both photofragment the target molecule and facilitate the detection of the characteristic NO fragment by REMPI and/or LIF via its $A^2\Sigma^+ - X^2\Pi_i$ transitions.

It is a further object of the present invention to provide an apparatus capable of detecting the presence of nitrogen dioxide, dimethylnitramine, nitromethane, nitrobenzene, TNT, and RDX by monitoring the presence of the $NO_x$ (usually $NO_2$) moiety therein in the atmosphere or adsorbed on a substrate.

Still a further object of the present invention is to provide a laser-based detector which is rugged and mobile.

A further object of the invention is to provide a laser-based detector apparatus capable of detecting the presence of concealed energetic materials.

Other objectives of the present invention will be apparent from the following detailed description of the invention.

DETAILED DESCRIPTION OF THE INVENTION

The detection and monitoring of trace amounts of atmospheric vapors of military/security interest is a technological task of increasing significance. The present invention relates to the ultra-sensitive detection of these types of vapors, and specifically the vapors of atmospheric and surface adsorbed $NO_x$ containing compounds. These are compounds which include energetic materials, such as propellants, and explosives, and pollutants.

Many molecules, including energetic materials, are difficult to detect spectroscopically using ultraviolet-visible (UV-VIS) absorption or emission. The difficulty stems from the lack of distinguishing structure or the absence of any features in the UV-VIS spectral region. As a result, numerous other approaches were sought to overcome this obstacle. One of the successful approaches resulting from experimentation was found to involve the use of laser sensor technology to photodissociate the parent molecules into the characteristic fragments sought. These photo-fragments typically included di- and triatomics, as well as singular atoms. These fragments were then found to be readily identifiable in the UV-VIS spectral region.

The present invention, which encompasses the apparatus as well as the method for accomplishing the detecting of the presence of $NO_x$ containing compounds, employs a single laser operating at or near 226 nm. The novelty of the invention resides primarily in the use of one laser to serve the purpose of photofragmentation of the target molecule and to facilitate the detection of the characteristic NO fragment by REMPI and/or LIF via its $A^2\Sigma^+ - X^2\Pi_i$ transitions. More specifically, the invention herein facilitates the detection of the presence of atmospheric vapor of $NO_2$ containing compounds based on the 226 nm photolysis of target molecules. The characteristic NO fragments, formed from the rapid predissociation of $NO_2$, are subsequently detected using the same laser by REMPI and/or LIF via the transition set forth above.

Propellants, explosives, and nitro-pollutants contain molecules with characteristic functional groups, namely the $NO_x$ (usually $NO_2$) moiety bonded to either a carbon or nitrogen atom. These functional groups are weakly bound to the main skeletal portion of the parent molecule by approximately 40 to 50 kcal/mole, depending upon the specific molecule. It is this moiety which is responsible for the weak and structureless absorption feature observed in the UV region near 230 nm. Ultraviolet laser photodissociation of RDX, for instance, under collision-free conditions results in the production of $NO_2$ in the initial step of the photolysis. $NO_2$ may be detected by its prompt emission or by laser-induced fluorescence (LIF).

These methods of detecting $NO_2$ are inefficient since the absorbed radiation is radiated over a large spectral region, visible to near infrared. The radiative lifetime for these transitions is also long, approximately 50 to 120 microsec, which is indicative of a weak oscillator strength. In addition, the predissociation of $NO_2$ to $NO+O$ predominates over fluorescence at wavelengths less than 400 nm.

The use of the NO fragment is better suited for detection since it is readily formed from the predissociation of $NO_2$. Moreover, the radiative lifetime of NO, which is approximately 200 nanoseconds, is significantly shorter than that of $NO_2$ excited in the visible region. The NO fragment can be detected with a high degree of sensitivity and selectivity by (1+1) resonance-enhanced multiphoton ionization (REMPI) and/or LIF via its $A^2\Sigma^+ - X^2\Pi_i$ transition at or near 226 nm. Thus, one may employ a single laser set to 226 nm to perform parent photofragmentation and facilitate fragment detection. It is this theory which is the basis for the present invention.

The laser photodissociation and fragment detection technique claimed herein is most effective when coupled with pulsed molecular beam sampling since it improves greatly the selectivity over ambient sampling and sensitivity over continuous sampling. The molecules in the molecular beam are colder than those at ambient conditions since they are subject to a supersonic expansion into a vacuum through a pulsed, small-orifice, nozzle. Thus, they are produced in a few distinct ro-vibrational states, and as a result, their absorption spectrum is considerably less congested and easier to analyze. This procedure additionally minimizes, or eliminates, interference which may otherwise be present from other molecular rotational bands.

The present invention additionally employs a pulsed nozzle which greatly reduces the total gas throughput entering the analysis chamber while maintaining a high density of the test sample. Hence, the pumping requirements employed herein are reduced which allows for a more compact design for the apparatus herein.

The apparatus herein is employed in the following fashion. Traces of atmospheric vapors are placed in a sampling device. This may be accomplished by the vapors being sniffed using a conventional suction device. Alternatively, adsorbed solid thin films of the compounds may be volatilized by a laser (infrared or ultraviolet) via fiber optic means and then sniffed. The vapors pass through a pulsed valve which facilitates the supersonic expansion of the analyte and the air within which it is found. The analyte or target molecule, herein represented by $R-NO_2$, is first photolyzed using 226 nm radiation to $NO_2$, along with its corresponding companion radical, R. After photolysis, the $NO_2$ fragment is then detected within the same laser pulse by monitoring its predissociative product NO using (1+1) REMPI and/or LIF employing its $A^2\Sigma^+ - X^2\Pi_i$ transition (0,0) band near 226 nm. Thus, one laser tuned to 226 nm can be used for parent photofragmentation and fragment detection. Other vibronic $A^2\Sigma^+ - X^2\Pi_i$ bands, such as (n,m) where n,m is greater than or equal to zero can also be employed in the detection of the NO fragment.

More specifically, with reference to the laser fragmentation and detection described, the characteristic NO fragment is excited with the same 226 nm laser radiation via a single or two-photon process. After the absorption of a single photon, the excited NO molecule can relax back to the ground state by emitting quanta of radiation, fluorescence. It may also absorb another 226 nm photon and thus ionize. The fluorescence signal is detected with a photomultiplier tube (PMT) or optical multichannel analyzer, while the NO ions are monitored by a conventional ion detector (i.e., an ion multiplier such as a dynode, multichannel plate (MCP), channeltron, etc.) or an optogalvanic probe. The MCP detector may be employed with a time-of-flight (TOF) analysis. The resulting signals are then displayed and monitored in real-time via a digital oscilloscope. A computer may be employed to store, analyze, acquire data and/or display the same.

The present invention has been shown to be useful; moreover, the limits of detection for numerous compounds were determined as well. These limits are reported herein for $NO_2$, DMNA, nitromethane, nitrobenzene, TNT, and RDX—note FIG. 5.

The specific features of the present invention will be further set forth in the drawings and their detailed description set forth below.

DETAILED DESCRIPTION OF THE DRAWINGS

The drawings will be further discussed in order to provide a better understanding and description of the present invention.

Figure 1:
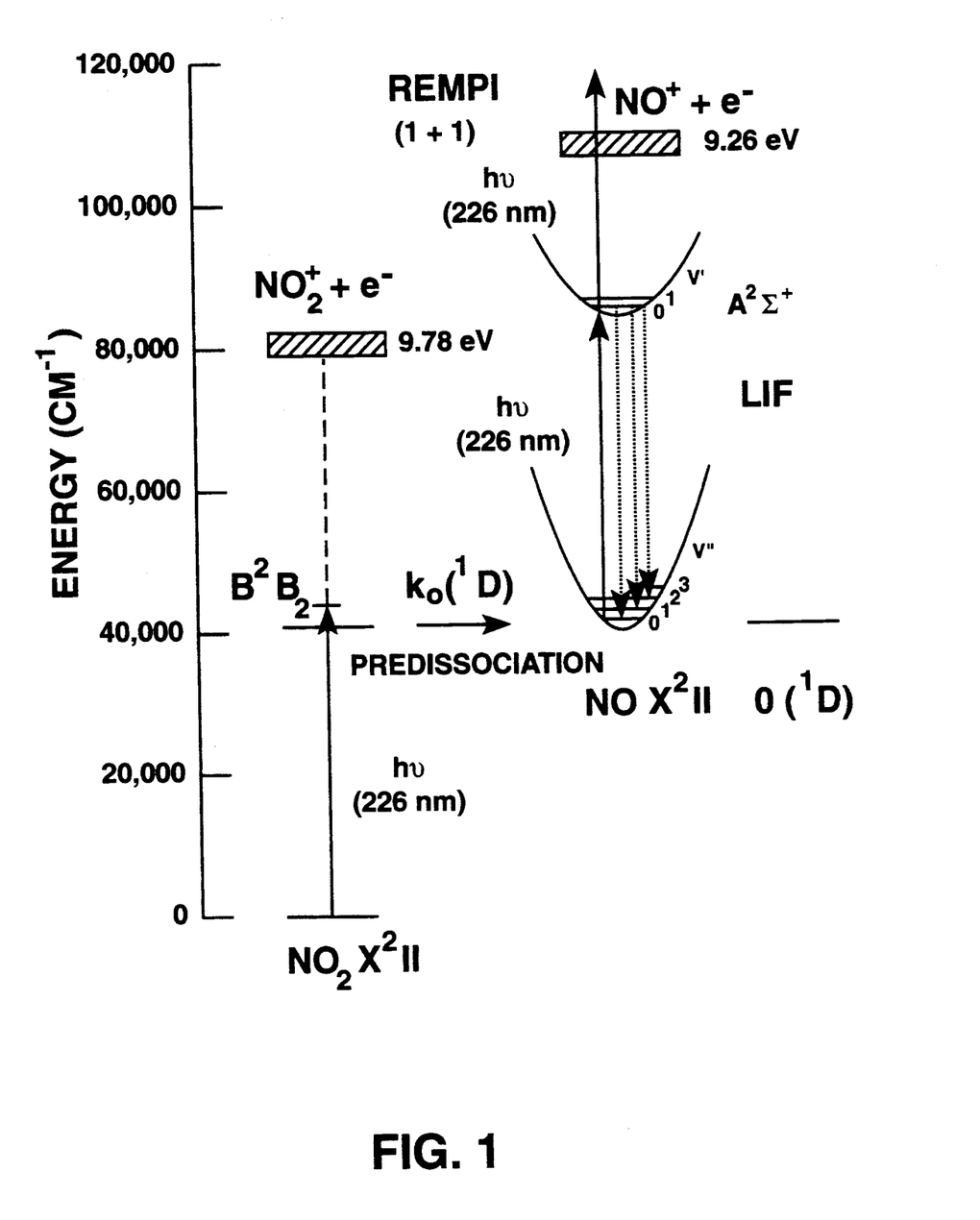
FIG. 1 is a potential energy diagram of $NO_2$ and NO showing the multiphoton scheme employed for the REMPI and/or LIF detection of the NO photofragment at or near 226 nm.

FIG. 1 illustrates the potential energy level diagrams of $NO_2$ and NO. The physical processes underlying the detection of these types of molecules within the present invention may be understood by reference to FIG. 1. In the present invention, the target molecule, $R-NO_2$, is first photolyzed to $NO_2$ along with its corresponding companion radical "R" via the process $$R-NO_2 \xrightarrow{h\nu}_{226\ nm} R + NO_2. \tag{1}$$

The $NO_2$ fragment is then detected by monitoring its predissociative product NO using (1+1) REMPI and/or LIF employing its $A^2\Sigma^+ - X^2\Pi_i(0,0)$ band near 226 nm. Therefore, a single laser tuned to 226 nm can be used for parent photofragmentation and fragment detection. The present invention may additionally be employed where other vibronic $A^2\Sigma + X^2\Pi_i$ bands, such as (n,m) where n,m are greater than or equal to zero, are used.

Figure 2A:
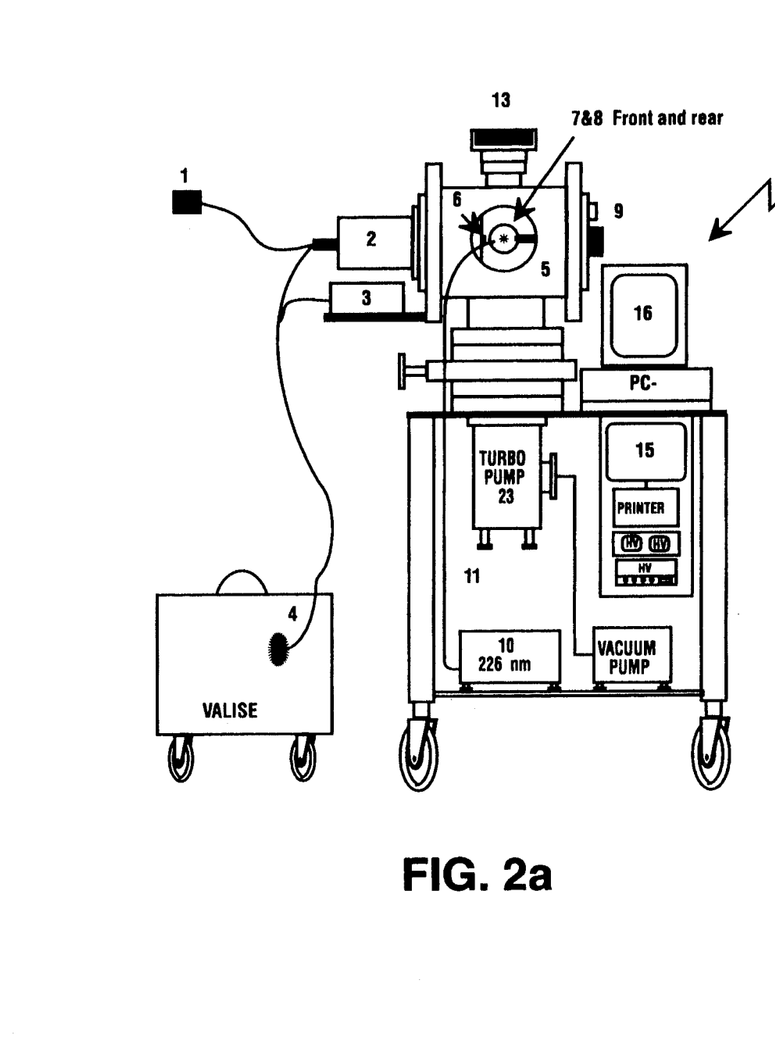
FIGS. 2a and 2b are schematic diagrams of the analyzer apparatus within the scope of the present invention.
Figure 2B:
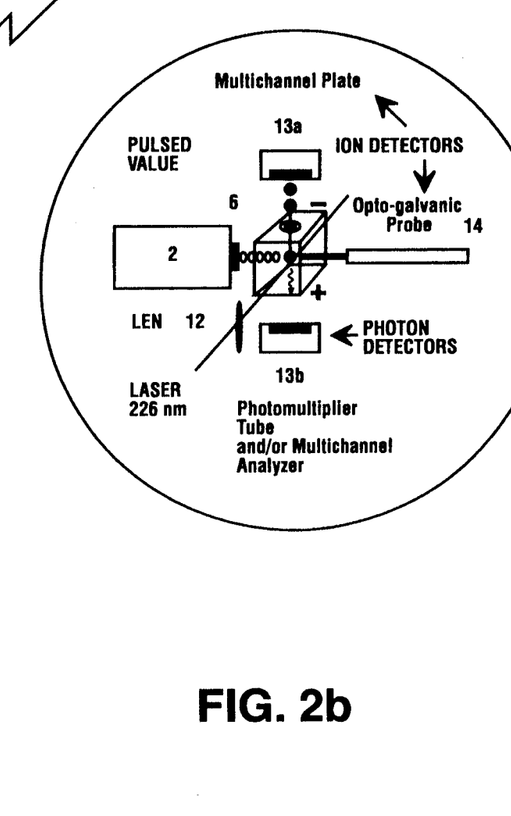

FIGS. 2a and 2b illustrate a schematic diagram of the trace explosive analyzer 21 within the scope of the present invention. The analyzer 21 is employed in the following fashion. Samples of trace atmospheric vapors are "sniffed" using a conventional suction device 1. The "sniffed" vapors are directed into the pulsed valve 2. Alternatively, adsorbed solid thin films may be volatilized into vapor form by a laser (IR or UV) 3, via fiber optic 4. This newly volatilized vapor may then subsequently be "sniffed" in the manner described above. As an aside, thermal and/or charged particle sources may also be employed to volatilize and/or fragment adsorbed film into the vapor phase.

Pulsed valve 2 (i.e., pulsed supersonic valve by R. M. Jordan Co. of Grass Valley, Calif.) serves to supersonically expand the air and analyte mixture (vapor) into the analysis chamber 5. This is accomplished through small orifice nozzle 6. The apparatus is equipped with three ports 7, 8 and 9. Ports 7 and 8 being at the front and rear of analysis chamber 5; and port 9 being along its side. These ports 7, 8 and 9 are employed for laser excitation of target molecules and for pressure recording. Pressure recording is performed to make certain that the operating pressure of the mass spectrometer is not exceeded. Said analysis chamber 5 is pumped out through the bottom by a 1,000 liter/second turbo pump 23 (i.e., Leybold-Heraeus, TurboVac 1000 of Brewster, N.Y. (USA Eastern Regional)) coupled to a rotary vane pump. Other pulsed valves and/or pumping systems may be employed herein.

The target molecules are then photolyzed by UV laser 10 with 226 nm of radiation being transmitted via fiber optic 11. A UV lens 12 may be employed in order to focus the laser beam from laser 10. After photolysis, the characteristic NO fragment is excited with the same laser radiation by a single or two-photon process. The excitation can result in either fluorescence, ionization, or both. A conventional ion multiplier (multichannel plate (MCP) detector) 13a or an optogalvanic probe 14 is used to detect the ion signal, while a photodetector (photomultiplier tube and/or optical multichannel analyzer 13b equipped with an appropriate interference filter) is used to detect the fluorescence signal. For the purposes of demonstration, the MCP detector 13a with time-of-flight analysis was employed—i.e., a commercial time-of-flight mass spectrometer, such as that manufactured by R. M. Jordan Co., may be employed. A photomultiplier tube is also employed to monitor the NO fluorescence signal. The signal observed by the detector 13a or 13b is displayed and monitored in real-time on a digital oscilloscope 15. A PC-AT computer 16 is employed for data acquisition, storage, analysis, and display.

For a time-of-flight spectrometer, the time of arrival, $t_1$, of mass, $m_1$, is related to the time of arrival, $t_2$, of mass, $m_2$, by the equation, $$m_1/m_2 = t_1/t_2 \qquad (2)$$

The determination of any mass, $m_2$, may be made with an accurate measurement of $t_1$ for a known mass, $m_1$. In this study, NO was used for the calibration of the mass spectra. For a typical set of operating conditions, a complete mass spectrum of up to 500 AMU could be recorded in approximately 70 microseconds.

Figure 3:
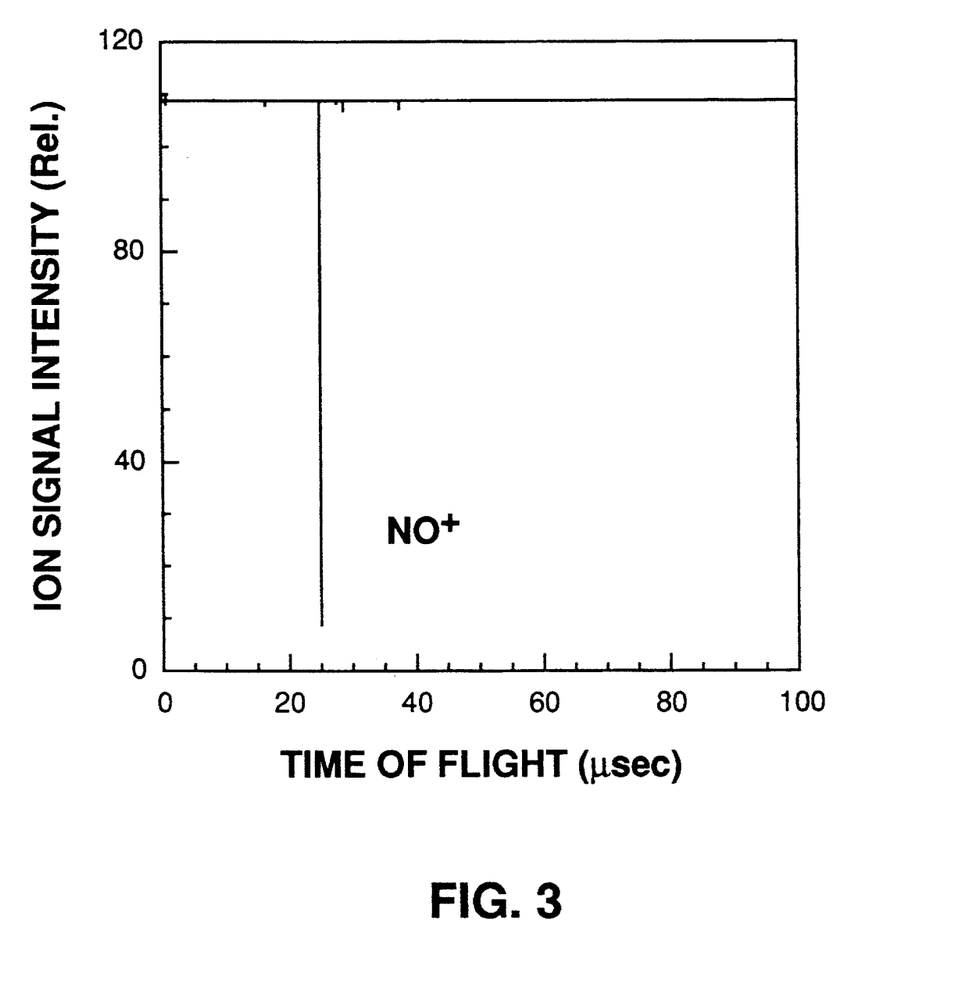
FIG. 3 is a time-of-flight REMPI mass spectrum of $NO^+$ generated from dimethylnitramine (DMNA) seeded in argon.

FIG. 3 is a mass spectrum obtained when photolyzing a molecular beam of DMNA seeded in argon using 226 nm radiation. This spectrum was found to be characteristic of all the compounds studied—i.e. see FIG. 5. The molecular beam was obtained by flowing argon gas at approximately one atmosphere over the vapor of the target compound and expanding the resulting gas mixture into the analysis chamber. The spectrum illustrated in FIG. 3 reveals a prominent peak wherein the arrival time to the detector is measured as 23.2 microseconds. This time corresponds to a mass-to-charge ratio of 30 and is attributed to the NO+ ion. (This ratio is the same as that of the NO ion and is the basis for its identification—i.e. N=14 AMU and O=16 AMU, hence NO=30 AMU.) Similar results were obtained when using air or nitrogen as the carrier gas. No such peak was observed, however, when the laser was tuned out of resonance with a molecular transition of NO. The observed peak is void of any interference and is clearly a result of a REMPI process. To maximize the signal intensity and verify the mass spectral assignment, an excitation spectrum was obtained by scanning the UV radiation while monitoring the m/e=30 peak. The spectrum revealed numerous rotational lines which are attributed unequivocally to electronic transitions of the NO $A^2\Sigma^+ - X^2\Pi_i$ (0,0) band.

Figure 4:
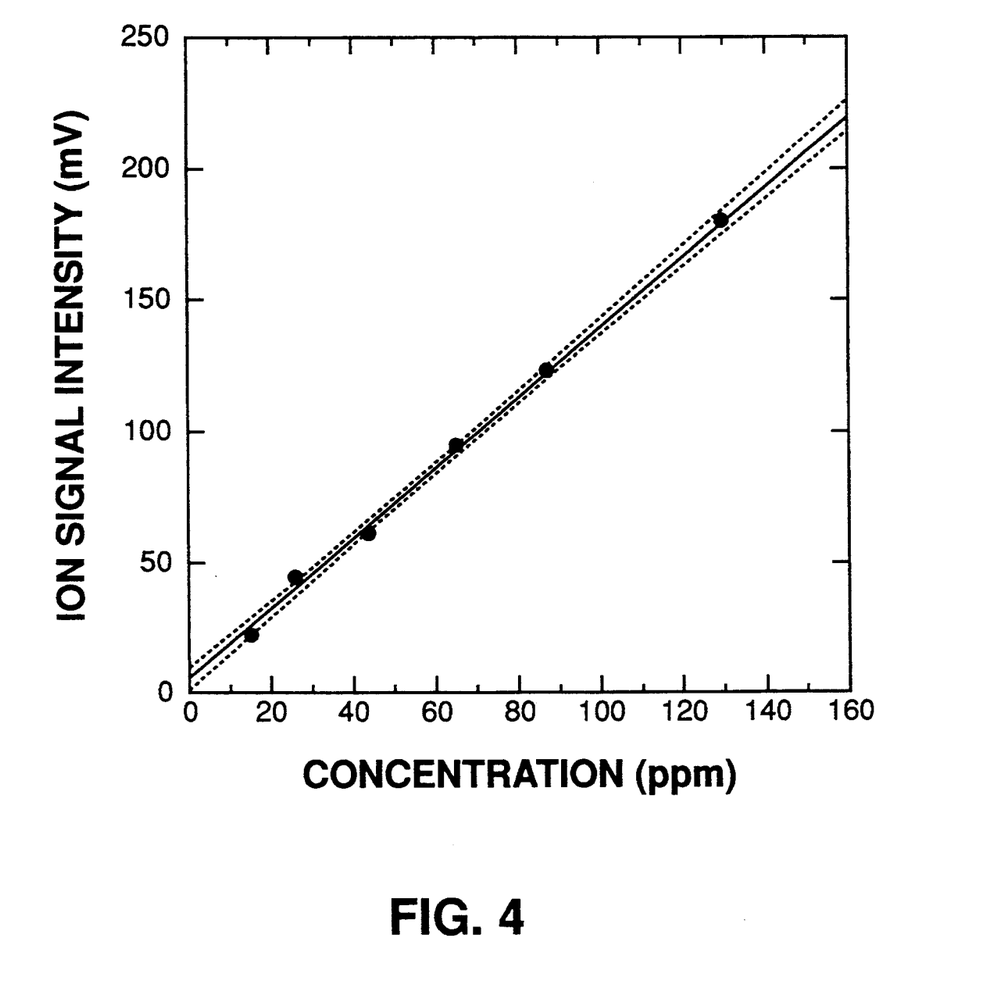
FIG. 4 is a plot of concentration vs. ion signal intensity of NO from DMNA.
Figure 5:
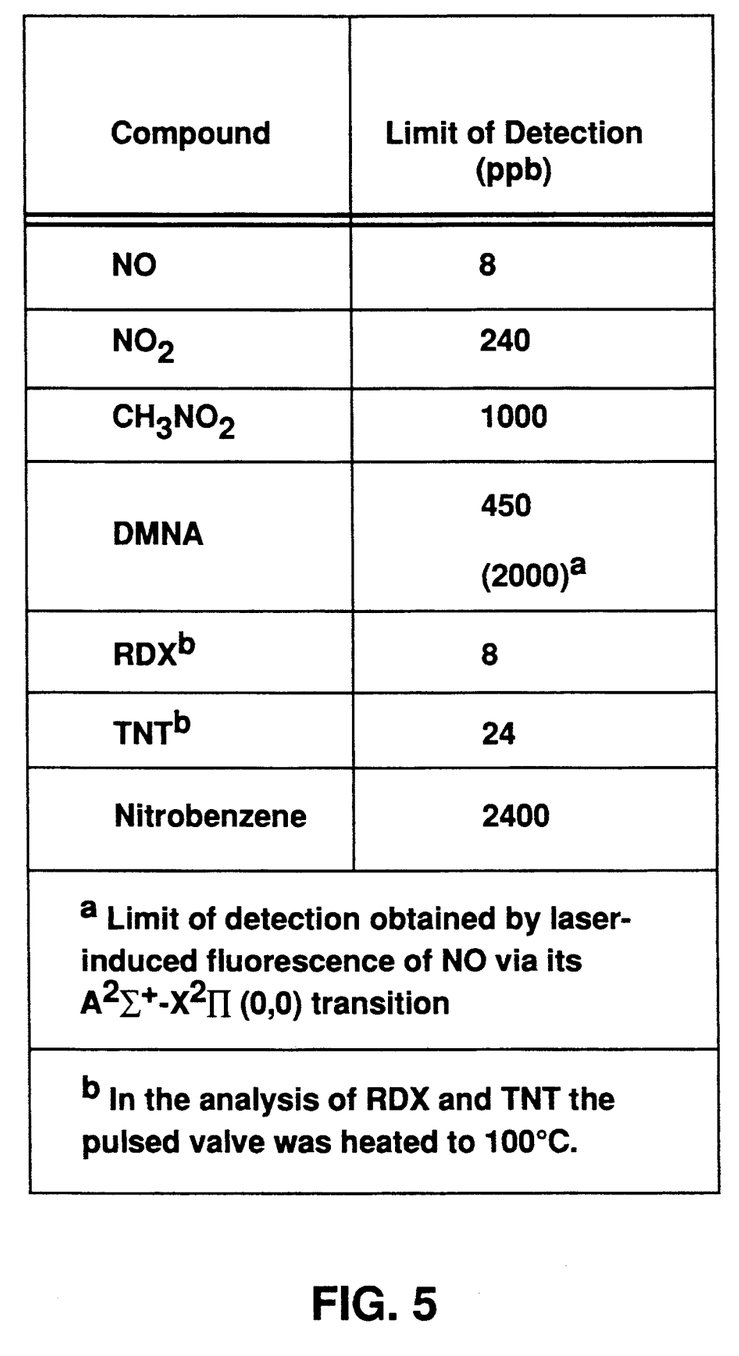
FIG. 5 is a chart which indicates the limits of detection for various $NO_2$ containing compounds tested employing the apparatus and method within the scope of the present invention.

Studies were conducted to determine the dependence of concentration and laser energy on signal intensity. FIG. 4 illustrates the concentration dependence of the REMPI NO+ ion signal obtained using DMNA. The figure is a plot of concentration vs. ion signal intensity. It reveals a linear relationship with the slope having a sensitivity value of 1.34 plus or minus 0.04 (2 SD) mV/ppm. The linearity of the relationship implies that the method employed is suitable for quantification purposes and that the NO is formed in a collision-free environment. A limit of detection of 450 ppb is obtained when using a background noise of 20 microvolts. Detection limits are defined within the scope of the present invention by the relationship.

$$C_L = 3\sigma/S \qquad (3)$$

where $C_L$ is the concentration (ppb) of the analyte that produces a signal, mV, equal to three times the standard deviation $\sigma$ (mV) of the background divided by the sensitivity, S (mV/ppb), of the method to the compound. The limits of detection described refer to the concentration of the vapor prior to its introduction into the analyzer apparatus. Limits found for the detection of various compounds tested are set forth in FIG. 5 herein. These limits of detection are based on employing the apparatus of the present invention using approximately 226 nm radiation.

The detection limits set forth in FIG. 5 are estimates of the detection limits for several compounds studied employing the fragmentation/REMPI-TOF technique using 226 nm radiation. As previously stated, these limits refer to the gas concentration of the analyte prior to its introduction into the analysis chamber. These estimates are subject to numerous factors which must be taken into consideration, such as laser pulse energy, efficiency of sample introduction, voltage settings of the ion optics and detector, and photodissociation efficiency. All of these factors affect the rate of signal production. Detection limits in the ppb can be obtained with a relatively small amount of laser energy, approximately 100 micro-Joules. When the limits of detection set forth in FIG. 5 were determined, the difference in vapor pressure of the precursors was taken into account. Therefore, any difference shown in FIG. 5 results from the different absorption cross sections and the efficiency in the photodissociative pathways leading to the formation of NO in its $X^2\Pi_i$ ($v''=0$) vibronic state. It is clear that RDX and TNT are particularly efficient in generating REMPI signals.

The dependence of ion signal intensity on laser pulse energy was also determined for DMNA using the equation, $$S = C(I_{226})^n \qquad (4)$$

wherein S is the ion signal intensity, $I_{226}$ is the laser beam fluence, C is a system-dependent constant, and n is the number of photons required to produce the NO+ signal. The value of n may be determined from the slope of a log-log plot of the variables in equation 4. One might expect the value of n to be as high as four, two photons required to generate NO in its $X^2\Pi$ state and two photons to ionize it (see FIG. 1). However, the slope of the plot yielded a value of $n=1.62$ plus or minus 0.01 (2 SD). This indicates that the formation of the ion required at least two photons. This near quadratic dependence suggests that one or more of the intermediate photochemical steps necessary to generate NO+ from R—NO$_2$ is saturated.

Using equation 4 for extrapolation purposes, an increase in the laser intensity from 100 micro-Joules to 100 milli-Joules yields a signal that is as much as 72,000 times greater than the 450 ppb obtained for DMNA (see FIG. 5). This corresponds to a limit of detection of approximately 6 ppt. Sub-ppt are projected for RDX and TNT using a similar extrapolation.

The proposed laser photodissociation/fragment detection technique is intended to identify nitrocompounds as a class or group by detecting the presence of the specific NO fragment, not the parent molecule. One advantage of this technique is its high degree of selectivity for NO since it combines the REMPI method with TOF mass spectrometry. The overall selectivity of the laser ionization method is a multiplicative combination of the selectivity achieved by the laser excitation process and the selectivity achieved by the mass spectral device. As shown in FIG. 3, a high degree of selectivity is obtained by the REMPI method. When the laser excitation wavelength is tuned to a strong NO transition, the ionization of NO occurs virtually at the exclusion of any other species. The selectivity for the NO fragment is further enhanced by the use of a TOF mass spectrometer, which prevents detection of any spectral ionization interferences, except those which are also isobaric.

For the purposes of comparing the methods of REMPI and LIF photofragment detection, the NO fragment was monitored by LIF via its $A^2\Sigma^+ - X^2\Pi_i$ (0,0) band following the photolysis of DMNA with 226 nm radiation. As shown in FIG. 5, the limit of detection was estimated to be 2 ppm, a factor of approximately 4 worse than that obtained with the REMPI technique. The difference in sensitivity results primarily from a high background inherent in its LIF measurement. The selectivity can also be compared for the two methods, since they share a common wavelength of excitation at 226 nm. In this study, the selectivity of the LIF measurement is lower due to the relatively larger bandwidth of the monochromator and interference filter used, and is not necessarily characteristic of the LIF technique. The large bandwidth is needed, however, in order to collect the broadband fluorescence emission of NO and maintain a sufficient level of sensitivity.

The present invention, as set forth above, is a detection and monitoring apparatus and method used to detect trace atmospheric and surface-adsorbed nitrocompounds. This apparatus may be used as a stand alone detector or in conjunction with separating methods (such as gas or liquid chromatography or cryogenic sampling) if additional selectivity is required.

While particular embodiments of the present invention have been shown and described, it will be obvious to those skilled in the art that changes and modifications may be made without departing from this invention. Therefore, it is intended that the claims herein are to include all such obvious changes and modifications as fall within the true spirit and scope of this invention.

We claim:

1. A method for the detection of atmospheric and surface adsorbed nitrocompounds comprising
    isolating a sample from an atmosphere or surface;
    directing said isolated sample into a sampling chamber;
    irradiating said isolated sample within said sampling chamber with a laser having a wavelength output at or near 226 nm so as to photolyze said nitrocompounds to form an NO fragment and excite said fragment by a resonance one or two-photon process via $A^2\Sigma^+ - X^2\Pi_i$ transitions of said fragment to form an excited NO fragment or ion;
    detecting said excited NO fragment or ion using an ion detector and/or photodetector; and
    recording and monitoring the presence or absence of said nitrocompounds on a data acquisition and processing system.

2. A method in accordance with claim 1, wherein said nitrocompounds are propellants.

3. A method in accordance with claim 1, wherein said nitrocompounds are explosives.

4. A method in accordance with claim 1, wherein said nitrocompounds are pollutants.

5. A method in accordance with claim 1, wherein a suction device is employed to isolate said sample.

6. A method in accordance with claim 1, wherein said nitrocompounds are surface absorbed and a laser coupled to optical fibers is used to volatilize and isolate said sample.

7. A method in accordance with claim 1, wherein said ion detector comprises a multichannel plate, a dynode assembly, a channeltron or an optogalvanic probe.

8. A method in accordance with claim 1, wherein said photodetector comprises a photomultiplier tube or an optical multichannel analyzer equipped with an interference filter.

9. A method in accordance with claim 1, wherein said method additionally comprises separating components of said isolated sample, prior to its being directed into said sampling chamber, using a chromatograph or cryogenic sampler.

10. A method for detecting the presence or absence of atmospheric and surface adsorbed nitrocompounds comprising
    photofragmenting a sample to form an NO fragment;
    exciting the NO fragment;
    detecting the presence or absence of said NO fragment with an ion detector and/or a photodetector;
    wherein said photofragmentation and excitation are achieved by irradiating said sample with a laser set at or near 226 nm corresponding to $A^2\Sigma^+ - X^2\Pi_i$ transitions of said fragment.

11. A method in accordance with claim 10, wherein said nitrocompounds are propellants.

12. A method in accordance with claim 10, wherein said nitrocompounds are explosives.

13. A method in accordance with claim 10, wherein said nitrocompounds are pollutants.

14. A method in accordance with claim 10, wherein said ion detector comprises a multichannel plate, a dynode assembly, a channeltron or an optogalvanic probe.

15. A method in accordance with claim 10, wherein said photodetector comprises a photomultiplier tube or an optical multichannel analyzer equipped with an interference filter.

16. A method in accordance with claim 10, wherein said method additionally comprises separating components of said sample which may contain said nitrocompounds, prior to its photofragmentation, using a chromatograph or cryogenic sampler.

* * * * *